United States Patent [19]

Drabek et al.

[11] 4,130,655
[45] Dec. 19, 1978

[54] PESTICIDAL 2,2-DIMETHYL-3-ISOBUTYL-CYCLOPROPIONATES

[75] Inventors: Jozef Drabek, Allschwil; Saleem Farooq, Aesch; Laurenz Gsell, Füllinsdorf; Odd Kristiansen, Möhlin; Willy Meyer, Riehen, all of Switzerland

[73] Assignee: Ciba-Geigy Corporation, Ardsley, N.Y.

[21] Appl. No.: 812,088

[22] Filed: Jul. 1, 1977

[30] Foreign Application Priority Data

Jul. 12, 1976 [CH] Switzerland ............ 8901/76
Apr. 27, 1977 [CH] Switzerland ............ 5218/77

[51] Int. Cl.² ............ A01N 9/20; A01N 9/24; C07C 69/74; C07C 121/75
[52] U.S. Cl. ............ 424/304; 260/465 D; 424/305; 560/124
[58] Field of Search ............ 260/465 D; 560/124; 424/304, 305

[56] References Cited

U.S. PATENT DOCUMENTS

| 3,835,176 | 9/1974 | Matsuo et al. ............ 260/465 D |
| 3,979,424 | 9/1976 | Elliott et al. ............ 560/124 X |
| 4,024,163 | 5/1977 | Searle et al. ............ 560/124 |

FOREIGN PATENT DOCUMENTS

| 2231312 | 1/1973 | Fed. Rep. of Germany. |
| 2432951 | 1/1975 | Fed. Rep. of Germany. |
| 2025534 | 9/1970 | France. |
| 1296088 | 11/1972 | United Kingdom. |

Primary Examiner—Dolph H. Torrence
Attorney, Agent, or Firm—Harry Falber

[57] ABSTRACT 2,2-Dimethyl-3-isobutyl-cyclopropionates of the formula

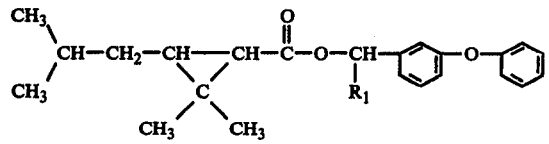

wherein $R_1$ represents cyano or ethynyl, processes for producing them and their use in combating pests.

5 Claims, No Drawings

PESTICIDAL 2,2-DIMETHYL-3-ISOBUTYL-CYCLOPROPIONATES

The present invention relates to 2,2-dimethyl-3-isobutyl-cyclopropionates of the formula

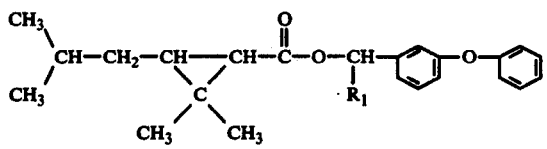

wherein $R_1$ represents cyano or ethynyl; to processes for producing them; and to their use in combating pests.

The compounds of the formula I are produced by methods known per se, for example as follows:

1)
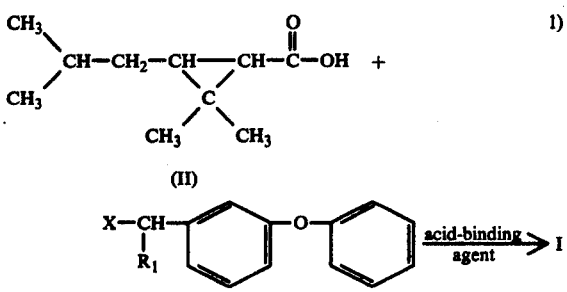

2)
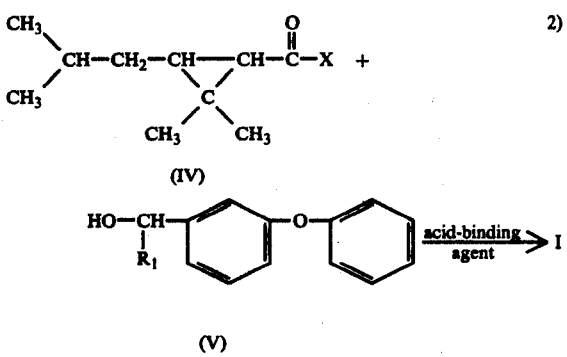

3)
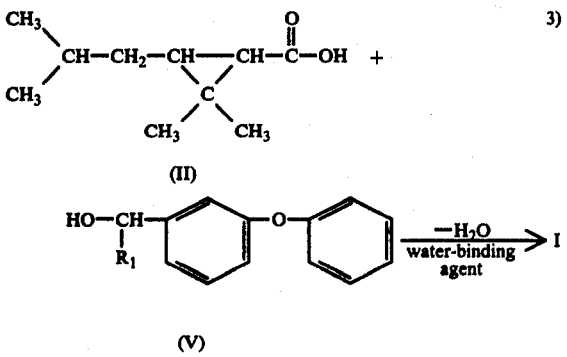

4)
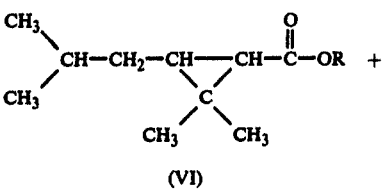

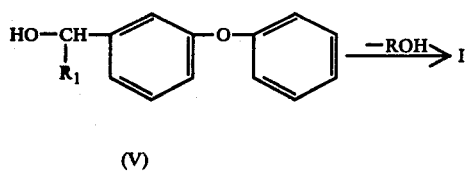

In the formulae III and V, $R_1$ has the meaning given under the formula I.

In the formulae III and IV, X represents a halogen atom, particularly chlorine or bromine; and in the formula VI, R represents $C_1$-$C_4$-alkyl, especially methyl or ethyl. Suitable acid-binding agents for the processes 1 and 2 are, in particular, tertiary amines such as trialkylamines and pyridine; also hydroxides, oxides, carbonates and bicarbonates of alkali metals and alkaline-earth metals, as well as alkali metal alcoholates such as potassium-t.-butylate and sodium methylate. The water-binding agent used for the process 3 can be, for example, dicyclohexylcarbodiimide. The processes 1 to 4 are performed at a reaction temperature of between $-10°$ and $100°$ C., usually between $20°$ and $80°$ C., under normal or elevated pressure and preferably in an inert solvent or diluent. Suitable solvents or diluents are, for example, ethers and ethereal compounds such as diethyl ether, dipropyl ether, dioxane, dimethoxyethane and tetrahydrofuran; amides such as N,N-dialkylated carboxylic acid amides; aliphatic, aromatic as well as halogenated hydrocarbons, particularly benzene, toluene, xylene, chloroform and chlorobenzene; nitriles such as acetonitrile; dimethylsulphoxide and ketones such as acetone and methyl ethyl ketone. The process 2 can also be performed in aqueous solution.

The starting materials of the formulae II to VI are known or can be produced by methods analogous to known methods. One method for producing the compound of the formula II is described in Example 1.

The compounds of the formula I are obtained as mixtures of various optically active isomers unless the starting materials used to produce the said compounds are homogeneous optically active materials. The different isomeric mixtures can be separated by known methods into the individual isomers. By compounds of the formula I are meant both the individual isomers and mixtures thereof.

The compounds of the formula I are suitable for combating various animal and plant pests. They can thus be used for combating representatives of phytopathogenic mites, for example of the genera Tetranychus and Panonychus; and also ticks and mites of the families Dermanyssidae and Ixodidae. They are particularly suitable however for combating insects of, e.g., the families Tettigoniidae, Gryllidae, Gryllotalpidae, Blattidae, Reduviidae, Pyrrocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae and Pulicidae.

The compounds of the formula I are particularly suitable for combating insects that damage plants, especially insects that damage plants by eating, in crops of ornamental plants and useful plants, particularly in cotton crops (e.g. against *Spodoptera littoralis* and *Heliothis virescens*) and in crops of vegetables (e.g. against

*Leptinotarsa decemlineata* and *Myzus persicae*). Active substances of the formula I also have a very favourable action against flies, such as *Musca domestica*, and against mosquito larvae.

The acaricidal and insecticidal action can be substantially broadened and adapted to suit given circumstances by the addition of other insecticides and/or acaricides. Suitable additives are, e.g., organic phosphorus compounds; nitrophenols and derivatives thereof; formamidines; ureas; other pyrethrin-like compounds; as well as carbamates and chlorinated hydrocarbons.

Compounds of the formula I are combined particularly advantageously also with substances which have a synergistic or intensifying effect on pyrethroids. Examples of such compounds are, inter alia, piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulphonyl)-propyl)-benzene.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:

solid preparations: dusts, scattering agents, granules, (coated granules, impregnated granules and homogeneous granules);
liquid preparations
(a) water-dispersible concentrates of active substance: wettable powders, pastes or emulsions;
(b) solutions.

The content of active substance in the described compositions is between 0.1 and 95%; it is to be mentioned in this respect that with application from an aeroplane, or from other suitable devices, concentrations of up to 99.5% or even the pure active substance can be used.

The active substances of the formula I can be formulated for example as follows: (parts are by weight):

Dusts

The following substances are used to produce (a) a 5% dust and (b) a 2% dust:

(a)

5 parts of active substance,
95 parts of talcum;

(b)

2 parts of active substance,
1 part of highly dispersed silicic acid,
97 parts of talcum.

The active substance is mixed and ground with the carriers.

Granulate

The following ingredients are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3 - 0.8 mm).

The active substance is mixed with epichlorohydrin and dissolved with 6 parts of acetone; the polyethylene glycol and cetyl polyglycol ether are then added. The solution obtained is sprayed onto kaolin and the acetone is evaporated off in vacuo.

Wettable powder

The following constituents are used to produce (a) a 40%, (b) and (c) a 25%, and d) a 10% wettable powder:

(a)

40 parts of active substance,
5 parts of sodium lignin sulphonate,
1 part of sodium dibutyl-naphthalene sulphonate,
54 parts of silicic acid;

(b)

25 parts of active substance,
4.5 parts of calcium lignin sulphonate,
1.9 parts of Champagne chalk/hydroxyethyl cellulose mixture (1:1),
1.5 parts of sodium dibutyl-naphthalene sulphonate,
19.5 parts of silicic acid,
19.5 parts of Champagne chalk,
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce (a) a 10%, (b) a 25%, and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)

25 parts of active substance,
2.5 parts of epoxidised vegetable oil, 10 parts of alkylarylsulphonate/fatty alcohol polyglycol ether mixture,
5 parts of dimethylformamide,
57.5 parts of xylene;

(c)

50 parts of active substance,
4.2 parts of tributylphenol-polyglycol ether,
5.8 parts of calcium-dodecylbenzenesulphonate,
20 parts of cyclohexanone,
20 parts of xylene.

Emulsions of the required concentration can be prepared from these concentrates by dilution with water.

Spray

The following constituents are used to produce (a) a 5% spray and (b) a 95% spray:

(a)

5 parts of active substance,
1 part of epichlorohydrin,
94 parts of ligroin (boiling limits 160°-190° C.);

(b)

95 parts of active substance,
5 parts of epichlorohydrin.

The invention is further illustrated by the following Examples.

EXAMPLE 1

Production of α-cyano-3-phenoxy-benzyl 2,2-dimethyl-3-isobutylcyclopropionate 2.6 g of pyridine in 10 ml of benzene is added dropwise to a solution of 6.75 g of α-cyano-3-phenoxy-benzyl alcohol in 40 ml of benzene, and subsequently there is added dropwise, at a temperature of 5°-10° C., the chloride of 2,2-dimethyl 3-isobutylcyclopropionic acid, which has been produced by 4 hours' boiling of 5.1 g of 2,2-dimethyl-3-isobutylcyclopropanecarboxylic acid and 5.1 g of thionyl chloride. The reaction mixture is then stirred for 2 hours and afterwards allowed to stand for 12 hours. In further processing, the reaction mixture is poured into ice water. The organic phase is washed with 1% hydrochloric acid, twice with water and twice with 5% sodium bicarbonate solution and dried. On removal of the benzene by distillation, there is obtained the compound of the formula

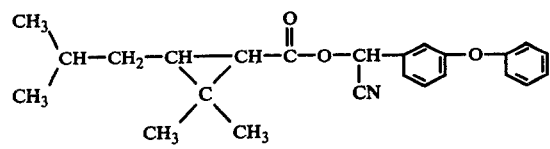

having a refractive index of $n^{20}_D = 1.5307$.

The following compound is produced in an analogous manner:

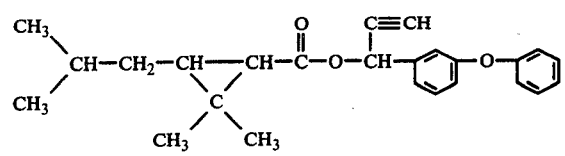

$n^{20}_D = 1.5327$

EXAMPLE 2

(A) Insecticidal stomach-poison action

Tobacco and potato plants were sprayed with a 0.05% aqueous active-substance emulsion (obtained from a 10% emulsifiable concentrate).

After drying of the coating, caterpillars of *Spodoptera littoralis* in the $L_3$-stage and of *Heliothis virescens* in the $L_3$-stage were placed onto the tobacco and potato plants. The test was carried out at 24° C. with 60% relative humidity.

The compounds according to Example 1 exhibited in the above test a good insecticidal stomach poison action against *Spodoptera littoralis* and *Heliothis virescens* caterpillars.

(B) Insecticidal contact action

One day before application of the active-substance emulsion, broad beans (*Vicia faba*) grown in pots were infested with about 200 bean aphids (*Aphis fabae*) per plant. The spray emulsion at a concentration of 1000 ppm (prepared from a 25% wettable powder) was applied by means of a compressed-air sprayer to the leaves infested with aphids. An evaluation was made 24 hours after application. The compounds according to Example 1 exhibited in the above test a good contact action against Aphis fabae.

We claim:

1. A compound of the formula

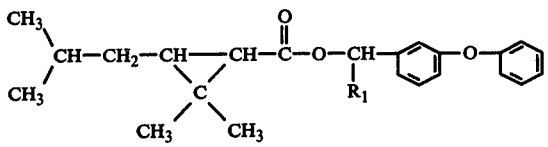

wherein $R_1$ represents cyano or ethynyl.

2. The compound according to claim 1 of the formula

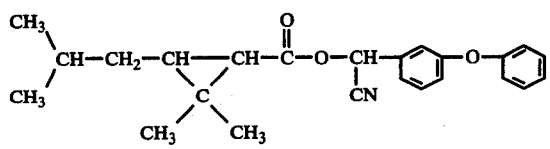

3. The compound according to claim 1 of the formula

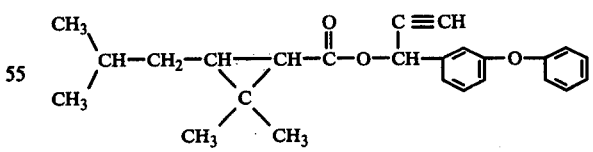

4. An insecticidal and acaricidal composition comprising an insecticidally or acaricidally effective amount of a compound according to claim 1, together with a suitable carrier therefor.

5. A method for combatting insects and acarids which comprises applying to the locus thereof an insecticidally or acaricidally effective amount of a compound according to claim 1.

* * * * *